United States Patent [19]
Modrich et al.

[11] Patent Number: 5,922,539
[45] Date of Patent: Jul. 13, 1999

[54] METHODS FOR USE OF MISMATCH REPAIR SYSTEMS FOR THE DETECTION AND REMOVAL OF MUTANT SEQUENCES THAT ARISE DURING ENZYMATIC AMPLIFICATION

[75] Inventors: Paul L. Modrich, Chapel Hill; Jane E. Smith, Durham, both of N.C.

[73] Assignee: Duke University, Durham, N.C.

[21] Appl. No.: 08/767,258

[22] Filed: Dec. 13, 1996

Related U.S. Application Data

[60] Provisional application No. 60/008,673, Dec. 15, 1995.
[51] Int. Cl.$^6$ .............................. C12Q 1/68; C07H 21/04; C12N 9/10
[52] U.S. Cl. ............................. 435/6; 435/91.1; 435/91.2; 435/183; 435/193; 435/810; 536/23.1; 536/24.3
[58] Field of Search .............................. 435/6, 91.1, 91.2, 435/183, 193, 810; 536/23.1, 24.3

[56] References Cited

U.S. PATENT DOCUMENTS 5,556,750   9/1996   Modrich et al. ............................. 435/6

OTHER PUBLICATIONS

Hsu et al., Detection of DNA point mutations with DNA mismatch repair enzymes, Carcinogenesis, vol. 15 (8), pp. 1657–1662, Aug. 1994.
Cormack. Mutagenesis by the Polymerase Chain Reaction. Current Protocols in Molecular Biology (F.A. Ausubel et al.) pp. 8.5.1–8.5.9. 1991.
Au et al., "Initiation of Methyl–directed Mismatch Repair," *J. Biol. Chem.* 267(17):12142–12148 (1992).
Bebenek and Kunkel, "Analyzing Fidelity of DNA Polymerases," *Methods in Enzymology* 262:217–232 (1995).
Eckert and Kunkel, "High fidelity DNA synthesis by the *Thermus aquaticus* DNA polymerase," *Nucleic Acids Research* 18:3739–3744 (1990).
Fersht, "Fidelity of replication of phage øX174 DNA by DNA polymerase III holoenzyme: Spontaneous mutation by misincorporation," *Proc. Natl. Acad. Sci. USA* 76:4946–4950 (1979).
Grilley et al., "Isolation and Characterization of the *Escherichia coli mutL* Gene Product," *J. Biol. Chem.* 264(2):1000–1004 (1989).
Innis et al., "DNA sequencing with *Thermus aquaticus* DNA polymerase and direct sequencing of polymerase chain reaction–amplified DNA," *Proc. Natl. Acad. Sci. USA* 85:9436–9440 (1988).
Ivey–Hoyle and Steege, "Mutational Analysis of an Inherently Defective Translation Initiation Site," *J. Mol. Biol.* 224:1039–1054 (1992).
Keohavong and Thilly, "Fidelity of DNA polymerases in DNA amplification," *Proc. Natl. Acad. Sci. USA* 86:9253–9257 (1989).
Kunkel and Loeb, "On the Fidelity of DNA Replication," *J. Biol. Chem.* 254:5718–5725 (1979).
Lahue et al., "DNA Mismatch Correction in a Defined System," *Science* 245:160–164 (1989).
Lehman and Nussbaum, *J. Biol. Chem.* 339:2628 (1964).
Little, *J. Biol. Chem.* 242:679 (1967).
Lundberg et al., "High–fidelity amplification using a thermostable DNA polymerase isolated from *Pyrococcus furiosus*," *Gene* 108:1–6 (1991).
Luria and Delbrück, "Mutations of Bacteria from Virus Sensitivity to Virus Resistance," *Genetics* 28:491–511 (1943).
Matteson et al., "Distinctive patterns of translational reinitation in the lac represso mRNA: bridging of long distances by out–of–frame translation and RNA secondary structure, effects of primary sequence," *Nucleic Acids Research* 19:3499–3506 (1991).
Mattila et al., "Fidelity of DNA synthesis by the *Thermococcus litoralis* DNA polymerase—an extremely heat stable enzyme with proofreading activity," *Nucleic Acids Research* 19:4967–4973 (1991).
Messing, "New M13 Vectors for Cloning," *Methods in Enzymology* 101:20–78 (1983).
Parsons et al., "Hypermutability and Mismatch Repair Deficiency in RER$^+$Tumor Cells," *Cell* 75:1227–1236 (1993).
Saiki et al., "Primer–Directed Enzymatic Amplification of DNA with a Thermostable DNA Polymerase," *Science* 239:487–491 (1988).
Su and Modrich, "*Escherichia coli mutS*–encoded protein binds to mismatched DNA base pairs," *Proc. Natl. Acad. Sci. USA* 83:5057–5061 (1986).
Su et al., "Mispair Specificity of Methyl–directed DNA Mismatch Correction in Vitro," *J. Biol. Chem.* 263(14):6829–6835 (1988).
Tindall and Kunkel, "Fidelity of DNA Synthesis by the *Thermus aquaticus* DNA Polymerase," *Biochemistry* 27:6008–6013 (1988).
Welsh et al., "Isolation and Characterization of the *Escherichia coli mutH* Gene Product," *J. Biol. Chem.* 262(32):15624–15629 (1987).

*Primary Examiner*—Nancy Degen
*Assistant Examiner*—Andrew Wang
*Attorney, Agent, or Firm*—Lyon & Lyon LLP

[57] ABSTRACT

Method for removing DNA molecules containing one or more polymerase-generated mutations in a population of enzymatically amplified DNA duplexes comprising the steps of denaturing and reannealing the population of DNA duplexes, contacting the reannealled DNA duplexes with a mismatch repair system such that each strand is cleaved in DNA duplexes containing a base pair mismatch, and separating the cleaved DNA duplexes from uncleaved DNA duplexes.

16 Claims, 5 Drawing Sheets

METHODS FOR USE OF MISMATCH REPAIR SYSTEMS FOR THE DETECTION AND REMOVAL OF MUTANT SEQUENCES THAT ARISE DURING ENZYMATIC AMPLIFICATION

This application claims priority to Provisional Application Modrich et al., U.S. Ser. No. 60/008,673 filed Dec. 15, 1995, entitled METHODS FOR USE OF MISMATCH REPAIR SYSTEMS FOR THE DETECTION AND REMOVAL OF MUTANT SEQUENCES THAT ARISE DURING ENZYMATIC AMPLIFICATION.

This work was supported by the U.S. Government, namely Grant No. GM23719. The U.S. Government may have rights in this invention.

FIELD OF THE INVENTION

The present invention relates to methods for the detection and removal of mutant sequences in DNA molecules that are the product of enzymatic amplification.

BACKGROUND OF THE INVENTION

The following is a discussion of the relevant art, none of which is admitted to be prior art to the appended claims.

DNA polymerase errors occurring during PCR amplification result in the presence of mutations in the amplified product. This problem can be particularly acute with Taq DNA polymerase which lacks a proofreading exonuclease and has a base substitution error rate on the order of $1/10^4$ to $1/10^5$ nucleotides polymerized under PCR conditions (Eckert and Kunkel, *Nucleic Acids Res.*, 18:3739, 1990; Mattila et al.,*Nucleic Acids Res.*, 19:4967, 1991; Saiki et al., *Science*, 239:487, 1988; Tindall and Kunkel, *Biochemistry*, 27:6008, 1988). The significance of error rates of this magnitude has been pointed out by Keohavong and Thilly (Keohavong and Thilly, *Proc. Natl. Acad. Sci. U.S.A.*, 86:9253, 1989), who noted that at a misincorporation rate of $2/10^4$, $10^6$-fold (twenty cycle) amplification of a 100 base pair sequence yields a population of product molecules, each of which has an 80% probability of containing a mutation somewhere in its sequence (Keohavong and Thilly, supra). The frequency of polymerase errors during PCR can be estimated from equations 1 and 6 of Luria and Delbrück (Luria, S. E. & Delbrück, M. *Genetics* 28:491–511, 1943) as $$f = 2lNa \qquad \text{(Equation 1)}$$

where f is the expected fraction of product molecules that contain a mutation somewhere in their sequence, l is the length of the amplified segment in bp, N is the number of cycles, and a is the error rate for the polymerase expressed per nucleotide incorporated. This problem has been alleviated to some extent by identification of the thermostable Pfu and Tli (Vent™) DNA polymerases, which have proofreading activity and display a two to ten-fold improvement in fidelity relative to Taq (Lundberg et al., *Gene*, 108:1, 1991; Mattila et al., supra). However, given that the probability of polymerase misincorporation event per cycle is also proportional to the size of the sequence being amplified, polymerase-generated mutations remain a significant problem for extensive amplification of sequences in the kilobase range.

SUMMARY OF THE INVENTION

The current invention concerns detection and removal of mutant sequences in DNA molecules that are the product of enzymatic amplification. It is based on the use of mismatch repair reactions, such as the MutHLS reaction of *E. coli* which is responsible for the initiation of bacterial methyl-directed mismatch repair. The presence of a mismatch within DNA molecules provokes cleavage at a GATC sequence located in the vicinity of the mispair in a reaction that depends on MutH, MutL, MutS and ATP (Au et al., *J. Biol. Chem.*, 267:12142, 1992). Hemimethylated GATC is incised on the unmethylated strand. Heteroduplex DNAs devoid of GATC methylation have been reported to be subject to mismatch-provoked single and double strand cleavage at such sites with the latter reaction evident after prolonged incubation or elevated concentrations of MutH, MutL, and MutS proteins (Au et al., supra) (See FIG. 1). In the current invention single or double strand cleavage is utilized to detect the presence of mutants that are the result of enzymatic amplification. The double strand cleavage reaction can also be exploited to remove mutant sequences from a population of amplified molecules.

The present invention is applicable to enzymatically amplified populations of DNA molecules. Such methods include polymerase chain reaction (PCR), and reverse transcription/ polymerase chain reaction (RT/PCR).

If the current invention is to be utilized for the removal of mutations that are the result of enzymatic amplification, a sequence of interest is amplified (e.g. by PCR) for N cycles, where N is chosen so that the expected mutant fraction (estimated from the fidelity of the polymerase used and the size of the sequence being amplified according to equation 1, or estimated experimentally as detailed below) is appropriately small by the criteria outlined below. The subsequent denaturation and reannealing of an amplified population of molecules containing a small mutant fraction results in hybridization of the vast majority of mutant strands with a wild type product. Material produced by denaturation and reannealing in this manner is subjected to a double strand cleavage reaction, e.g., using the MutHLS cleavage reaction of *E. coli* (See FIG. 2), with prior removal of PCR primers and dNTPs as necessary (e.g., by gel filtration). The uncleaved fraction is comprised of molecules that are mismatch-free and hence greatly enriched in mutation-free sequences. Provided that N cycles yields sufficient material for analysis, the uncleaved fraction can be separated from cleaved, mutation-containing fragments by size separation (e.g., by electrophoresis through poly-acrylamide or agarose gels under non-denaturing conditions).

Since a PCR error can, in principle, occur at any position in a sequence undergoing amplification, the mutant fraction of an amplified product is expected to be comprised of a population of different mutations (the terms mutation or mutant as used in this paragraph refer to PCR-generated sequence changes). This population will represent possible set base pair changes that may occur at each position in the sequence undergoing amplification. Therefore, those product molecules containing a particular mutation (e.g., that resulting from a polymerase error at a particular base pair) will typically represent only a very small fraction of the total mutant population. Thus, denaturation and reannealing of a PCR product to itself, even at a relatively high mutant fraction (e.g. 50%) will result in the vast majority of a particular mutant strand hybridizing either to a non-mutant strand or to a strand that contains a distinct mutation. The former class of hybrid molecule will contain one mismatch and the latter two or more mispairs, and both classes of hybrid will be sensitive to attack by MutH, MutL, and MutS. Hence, both classes will be subject to elimination of the mutant sequences contained therein by the method described above. Since the *E. coli* methyl-directed repair system does not appear to process the C—C mismatch (Su, S.-S., Lahue, R. S., Au, K. G., and Modrich, P., *J. Biol. Chem.,* 263:68299–6835, 1988; Lahue, R. S., Au, K. G., and Modrich, P., *Science,* 245:160–164, 1989), this method will not remove those sequences in which the corresponding hybrid molecule contains only a C—C mispair.

Under certain conditions it may be desirable to restrict the number of cycles in order to yield a smaller mutant fraction (e.g. 10%). Certain types of amplification reaction are potentially subject to occurrence of a "jackpot" of a particular sequence change (Luria, S. E. & Delbruck, J., *Genetics,* 28:491–511, 1943). For example, during single molecule PCR (e.g., amplification reactions that start with only one or a few molecules of template) occurrence of a particular PCR-induced sequence change during an early cycle will lead to a high fraction of a particular mutation in the ultimate product because the mutant sequence will amplify exponentially during subsequent cycles.

The method for removal of PCR-induced mutant sequences described here is not restricted to amplification products derived from haploid genomes. The procedure can also be utilized with PCR products derived from diploid genomes, even when the cells of origin happen to be heterozygotic for one or more sequence differences within the region of interest (e.g., alleles A and a). Amplification of A sequences from an Aa heterozygote is expected to yield A and a products in near molar equivalence, plus PCR-generated mutant sequences derived from each allele. In addition to hybrid molecules containing mutant sequences, denaturation and reannealing of this product is expected to yield heteroduplexes with strand genotypes A:A, a:a, A:a, and a:A at expected ratios of 1:1:1:1. Like hybrid molecules containing PCR-induced mutations, A:a, and a:A heteroduplexes will also be subject MutH–, MutL–, and MutS– dependent, mismatch-provoked double strand cleavage. However, the desired products (A:A and a:a duplex DNAs which are expected to represent somewhat less than half of the total product) will be mismatch-free and refractory to attack by these activities.

If the original N cycles of PCR does not yield sufficient material for physical isolation of mutation-depleted population after MutHLS cleavage, and further amplification is required, the invention features two alternate approaches to handle mutant sequences so that polymerase-generated errors will not be propagated upon further amplification. These approaches are based on inactivation of the primer activity of cleavage products or the removal of cleavage products by an enzymatic procedure utilizing a combination of exonucleases.

MutHLS mediated cleavage at GATC sequences occurs 5' to the G (↓pGpApTpC); thus double strand products produced by this reaction possess a four nucleotide 5'-overhang analogous to that produced by many restriction endonucleases. Incubation of MutHLS reaction products with dideoxyguanosine-5'-triphosphate and a DNA polymerase able to add the dideoxynucleoside at the 3'-termini produced by mismatch provoked cleavage will inactivate the priming activity in subsequent PCR cycles. Although mutant sequences will remain in the population, they will amplify in a linear rather than an exponential fashion in subsequent PCR cycles. Other organisms may use an endonuclease with different cleavage specificity than MutH and thus would necessitate use of a dideoxynucleoside-5'-triphosphate other than dideoxyguanosine-5'-triphosphate.

An alternate enzymatic approach, physically removes mismatch repair reaction cleavage products containing mutant sequences. This method is based on the high specificity of certain exonucleases, such as λ exonuclease, for duplex DNA with 5'-phosphoryl termini (Little, *J. Biol. Chem.,* 242:679, 1967). The initial N cycles of PCR amplification are performed with primers containing 5'-hydroxyl termini. After amplification, denatured and reannealed products are treated with mismatch repair enzymes such as MutH, MutL, and MutS, as described above. Since GATC cleavage of mismatch-containing molecules results in products with 5'-phosphoryl termini, one strand of each double strand cleavage product is thus rendered sensitive to hydrolysis by λ exonuclease. The use of primers with 5'-hydroxyl termini prevents exonuclease attack of non-cleaved products. The remaining single strand is then removed by hydrolysis with single-strand specific exonuclease, such as exonuclease I (Lehman and Nussbaum, *J. Biol. Chem.,* 339:2628, 1964). After inactivation or removal of the two exonuclease activities (for example, by phenol extraction), the mutation-depleted fraction may be subjected to additional rounds of PCR with a subsequent MutHLS cleavage step used to remove mutant sequences.

The invention also features a method to directly estimate the fraction of PCR product molecules that contain a polymerase-induced mutation. After denaturation and reannealing and subsequent cleavage with mismatch repair enzymes, such as MutHLS, cleaved and uncleaved DNA duplexes are separated, e.g., by gel electrophoresis, and the relative amount of DNA duplexes present in each fraction is determined by standard techniques used for DNA quantitation. The extent of MutHLS cleavage at this point provides a direct estimate of the fraction of PCR product molecules that contain one or more polymerase-induced mutations.

The methods of the claimed invention require the presence of a sequence that is subject to mismatch provoked endonucleolytic cleavage, such as a dGATC site, in the sequence to be analyzed, so that endonucleolytic cleavage can occur. If such a site does not exists in the region that is amplified a sequence that is subject to mismatch provoked endonucleolytic cleavage can be introduced by using a primer that contains this sequence. Thus, the invention also features a method to detect or remove errors in sequences that do not contain a sequence that is subject to mismatch provoked endonucleolytic cleavage. Molecules without dGATC sites may be screened or removed with MutHLS cleavage by introducing a dGATC site into the primer used for amplification. Applicant has found that dGATC sites 50–100 bp from the end of a molecules are sufficient for mutation screening. Sequences other than GATC, that are subject to mismatch provoked endonucleolytic cleavage by mismatch repair enzymes from other organisms, can also be utilized in the present invention.

Other organisms, including man, are known to possess systems for recognition and repair of DNA mispairs, which, as one skilled in the art would appreciate, comprise proteins functionally homologous to the MutHLS proteins of *E. coli,* which may be used in the present invention.

Thus in a first aspect the invention features a method for removing DNA molecules containing one or more polymerase-generated mutations in a population of enzymatically amplified DNA duplexes. The method comprises denaturing and reannealing the population of DNA duplexes, contacting the reannealed DNA duplexes with a mismatch repair system such that each strand is cleaved in DNA duplexes containing a base pair mismatch, and separating said cleaved DNA duplexes from uncleaved DNA duplexes.

By "polymerase generated mutations" is meant a misincorporation of a nucleotide by a DNA polymerase during the course of DNA amplification, so as to produce incorrect pairing between the bases of two nucleotides located on complementary strands of DNA, i.e., base pairs that are not A:T or G:C, or the presence of 1, 2 or 3 extra unpaired, adjacent nucleotides on one strand (an insertion/deletion mismatch).

By "enzymatically amplified DNA duplexes" is meant DNA that has been amplified by an enzymatic amplification reaction. Examples of such reactions include the polymerase chain reaction and reactions utilizing reverse transcription and subsequent DNA amplification of one or more expressed RNA sequences.

By "denaturing and reannealing" is meant methods known to those who practice the art, by which the hydrogen bonding of DNA duplex molecules is sequentially disrupted and then allowed to reform. Preferred methods for denaturing and reannealing include elevation of temperature followed by lowering of temperature and elevation of pH (e.g., pH 13) followed by neutralization and annealing at an appropriate temperature. Alternative methods include use of enzymes such as RNase H in RT/PCR methodology.

By "mismatch repair system" is meant proteins that include a GATC endonuclease such E. coli MutH or a protein functionally homologous to E. coli MutH (the protein may cleave at a site different from GATC), a mispair recognition protein such E. coli MutS or a protein functionally homologous to E. coli MutS, and proteins that participate in the activation of the GATC endonuclease such as E. coli MutL or a protein functionally homologous to E. coli MutL, and necessary cofactors such as $MgCl_2$ and ATP.

By "separating" is meant isolating the cleaved molecules from uncleaved molecules by methods that achieve physical separation, such as electrophoresis or HPLC.

In preferred embodiments, the method of separation is by electrophoresis through a gel; the mismatch repair system comprises components of the methyl-directed mismatch repair system of E. coli and includes the Muts, MutL, and MutH proteins.

By "electrophoresis through a gel" is meant the method of size fractionation by electrophoretic mobility, a procedure well known by those skilled in the art. Gel electrophoresis can either be conventional or pulse-field.

The "components of the methyl-directed mismatch repair system of E. coli" includes the proteins MutH, MutL and MutS and cofactors $MgCl_2$ and ATP.

In a second aspect the invention features a method for removing DNA molecules containing one or more polymerase-generated mutations in a population of DNA duplexes that have been enzymatically amplified using primers containing 5'-hydroxyl termini. The method comprises denaturing and reannealing the population of DNA duplexes, contacting the reannealed DNA duplexes with a mismatch repair system such that each strand in DNA duplexes containing a base pair mismatch is cleaved so as to produce 5'-phosphate termini, and further contacting the population of reannealed DNA duplexes with exonucleases so that the DNA duplexes containing a base pair mismatch are enzymatically degraded.

The use of primers with 5'-hydroxyl termini prevent exonuclease attack at sites other than cleavage sites generated by the mismatch repair system. Primers are typically constructed with such 5'-hydroxyl termini.

By "exonucleases" is meant a combination of an exonuclease that preferentially degrades duplex DNA and also has a preference for 5'-phosphate, such as λ exonuclease, and a single strand specific exonuclease, such as exonuclease I.

By "enzymatically degraded" is meant broken down to single nucleotides or dinucleotides.

In a preferred embodiment, the mismatch repair system comprises components of the methyl-directed mismatch repair system of E. coli and includes the Muts, MutL, and MutH proteins.

In a third aspect the invention features a method for rending inert to further amplification DNA molecules containing one or more polymerase-generated mutations in a population of enzymatically amplified DNA duplexes. The method comprises denaturing and reannealing the population of DNA duplexes, contacting the reannealed DNA duplexes with a mismatch repair system such that each strand is cleaved in DNA duplexes containing a base pair mismatch, and, further contacting the cleaved DNA duplexes with dideoxynucleoside-5'-triphosphate and a DNA polymerase capable of adding a dideoxynucleoside-5'-monophosphate moiety to 3'-termini produced by mismatch-provoked cleavage.

By "inert to further amplification" is meant unable to be subject to further exponential amplification as the cleaved DNA molecules have incorporated a chain terminating nucleotide incapable of supporting further elongation.

By "dideoxynucleoside-5'-triphosphate" is meant a nucleoside-5'-triphosphate with the 3'-hydroxyl group replaced by a hydrogen so as to result in a chain terminating analog. This analog will block the growth of a new DNA chain as it lacks a 3'-hydroxyl necessary to form a phosphodiester bond.

In a preferred embodiment, the mismatch repair system comprises components of the methyl-directed mismatch repair system of E. coli and includes the Muts, MutL, and MutH proteins and the dideoxynucleoside-5'-triphosphate is dideoxyguanosine-5'-triphosphate.

In a fourth aspect the invention features a method for determining the fraction of an enzymatically amplified DNA population that contains polymerase-generated mutations. The method comprises denaturing and reannealing the population of DNA duplexes, contacting the reannealed DNA duplexes with a mismatch repair system such that at least one strand is cleaved in DNA duplexes containing a base pair mismatch, separating the cleaved DNA duplexes from uncleaved DNA duplexes, and determining the fraction of cleaved DNA duplexes relative to uncleaved DNA duplexes as an indication of the fraction of enzymatically amplified DNA that contain polymerase-generated mutations.

By "at least one strand is cleaved" is meant that an endonucleolytic incision is introduced into one or both strands of a DNA molecule containing a base pair mismatch. The length of incubation and the concentration of the mismatch repair enzymes determine whether one or two endonucleolytic incisions are introduced.

By "separating the cleaved DNA duplexes from uncleaved DNA duplexes" is meant the physical separation of the two classes of molecules and includes electrophoresis under denaturing conditions.

By "determining the fraction of cleaved DNA duplexes relative to uncleaved DNA duplexes" is meant detecting and quantitating DNA, after separation of the cleaved and uncleaved molecules, so that the relative amounts in each fraction can be determined. Detection and quantitation of DNA can be carried out by methods familiar to those who practice the art, utilizing known labeling, staining, and quantitation techniques for nucleic acids.

In a preferred embodiment, the mismatch repair system comprises components of the methyl-directed mismatch repair system of *E. coli* and includes the Muts, MutL, and MutH proteins.

In a fifth aspect, the invention features a method for detecting the presence of DNA polymerase-generated mutations in a population of enzymatically amplified DNA duplexes. The method comprises denaturing and reannealing the population of DNA duplexes, contacting the reannealed DNA duplexes with a mismatch repair system under conditions such that a duplex containing a polymerase generated mutation is modified by the introduction of an endonucleolytic incision in at least one strand of the duplex, and detecting the product of the endonucleclytic incision as an indication of the presence of polymerase generated mutations.

The endonucleolytic incision or cleavage product can be detected by any method which detects a difference between the incision product and an unmodified molecule. Such methods include those that detect differences in size or electrophoretic mobility.

In preferred embodiments, detection of the product of the endonucleolytic incision is by altered electrophoretic mobility under denaturing conditions; the mismatch repair system comprises components of the methyl-directed mismatch repair system of *E. coli* and includes the Muts, MutL, and MutH proteins.

By "altered electrophoretic mobility" is meant mobility on a gel that is different from or relatives to an unmodified, i.e., uncleaved molecule.

Denaturing conditions are know to those who practice the art, and include the use of urea.

In a sixth aspect, the invention features a method for detecting the presence of DNA polymerase-generated mutations in a population of enzymatically amplified DNA duplexes produced from DNA duplexes lacking a sequence subject to mismatch provoked endonucleolytic cleavage. The method comprises the steps of enzymatically amplifying a population of DNA molecules utilizing primers containing a sequence subject to mismatch provoked endonucleolytic cleavage, denaturing and reannealing the population of DNA duplexes, contacting the reannealed DNA duplexes with a mismatch repair system under conditions such that an endonucleolytic incision is introduced in at least one strand of a duplex containing a polymerase generated mutation, and detecting the product of the endonucleolytic incision as an indication of the presence of polymerase generated mutations.

By "primers that contain a sequence subject to mismatch provoked endonucleolytic cleavage" is meant primers engineered to contain a sequence that is specifically cleaved in response to the presence of a mismatch by components of a mismatch repair system. Primers with such sites can be constructed by standard cloning techniques known to those who practice the art.

The invention also features the use of primers containing a sequence subject to mismatch provoked endonucleolytic cleavage for the removal of DNA molecules containing one or more polymerase-generated mutations in a population of enzymatically amplified DNA duplexes produced from DNA duplexes lacking a sequence subject to mismatch provoked endonucleolytic cleavage. The method comprises the steps of enzymatically amplifying a population of DNA molecules utilizing primers containing a sequence subject to mismatch provoked endonucleolytic cleavage, denaturing and reannealing the population of DNA duplexes, contacting the reannealed DNA duplexes with a mismatch repair system under conditions such that each strand is cleaved in a DNA duplex containing a polymerase generated mutation, and separating the cleaved DNA duplexes from uncleaved DNA duplexes.

In preferred embodiments, the sequence subject to endonucleolytic cleavage is a d(GATC) site; detection of the product of endonucleolytic incision is by altered electrophoretic mobility under denaturing conditions; the mismatch repair system comprises components of the methyl-directed mismatch repair system of *E. coli* and includes the Muts, MutL, and MutH proteins.

In a seventh aspect, the invention features various kits for detecting, removing, or rendering inert to further amplification DNA molecules containing one or more polymerase-generated mutations in a population of enzymatically amplified DNA duplexes. One such kit useful for amplifying DNA molecules and for removing DNA molecules containing one or more polymerase-generated mutations in a population of enzymatically amplified DNA duplexes comprises primers with 5'-hydroxyl termini, components of a mismatch repair system, and exonucleases. Another kit for removing DNA molecules containing one or more polymerase-generated mutations in a population of enzymatically amplified DNA duplexes comprises components of a mismatch repair system and exonucleases. The invention also features a kit for rendering inert to further amplification DNA molecules containing one or more polymerase-generated mutations in a population of enzymatically amplified DNA duplexes comprising components of a mismatch repair system, a dideoxynucleoside-5'-triphosphate, and a DNA polymerase. Another kit is useful for amplifying DNA molecules lacking a sequence subject to mismatch provoked endonucleolytic cleavage and for detecting or removing DNA molecules containing one or more polymerase-generated mutations from this population of enzymatically amplified DNA duplexes. This kit comprises primers containing sequence subject to mismatch provoked endonucleolytic cleavage, and components of a mismatch repair system.

The present invention offers several advantages over other methods used to detect and/or eliminate polymerase-induced mutations in amplification reactions.

The reliability and applicability of molecular methods for mutation detection have been subject to technical limitations, high levels of background signal for perfectly paired DNA sequences and failure to detect all mutations. Methods relying solely upon differential resolution of DNA fragments in polyacrylamide gels are subject to severe size constraints. Chemical approaches to mutation detection are subject to background reactivity with perfectly paired sequences. Enzymatic methods have proven less robust in their sensitivity to different mutations and in some cases are subject to background signals with perfectly paired DNA. Mismatch repair systems, such as the MutHLS-dependent d(GATC) cleavage reaction, circumvent many of these limitations, as they are exquisitively sensitive to the presence of mismatches and have a high degree of accuracy.

Polymerases with high efficiency and/or proof reading capacity are limited in their ability to reduce the number of polymerase-generated errors as the probability of a polymerase misincorporation event increases as does the number of amplification cycles and is proportional to the size of the sequence being amplified. In distinction, the methods of the present invention are not subject to these limitations as they are utilized after the amplification event. In addition, as these methods are based on the use of extremely sensitive and accurate mispair recognition proteins, most errors should be detected and eliminated, regardless of the number of cycles or the size of the amplified sequence. The notable exception is C—C mismatches, which are not recognized by the *E. coli* methyl-directed system.

Other features and advantages of the invention will be apparent from the following description of the preferred embodiments thereof, and from the claims.

DESCRIPTION OF THE PREFERRED EMBODIMENTS

Figure 1:
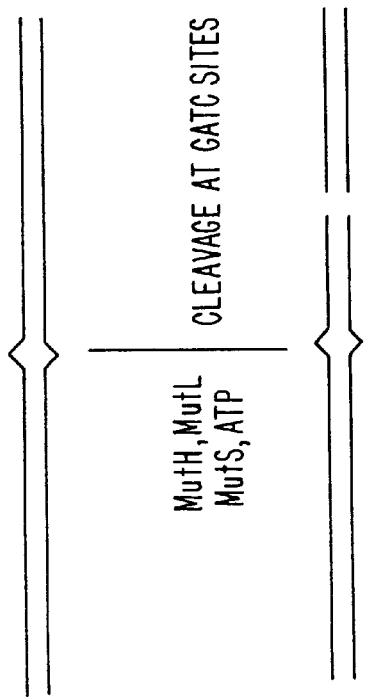
FIG. 1 is a schematic representation of the MutHLS double strand cleavage reaction.
Figure 2:
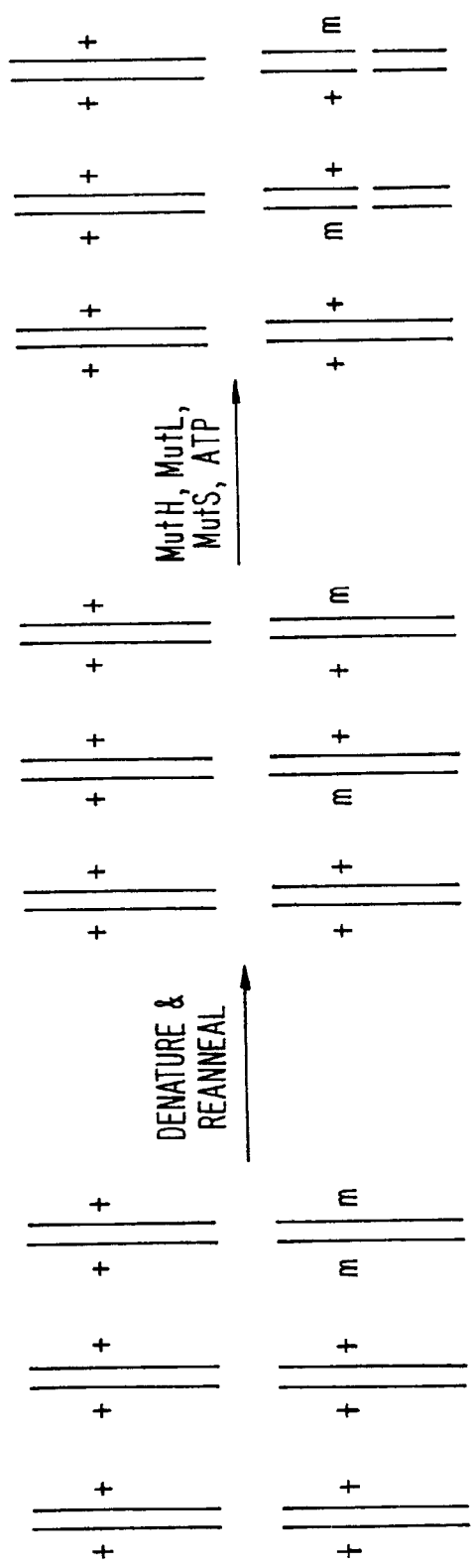
FIG. 2 is a schematic representation of denaturation and reannealing of an enzymatically applied population followed by the MutHLS double strand cleavage reaction of molecules containing a base pair mismatch.

The current invention encompasses methods for the detection and removal of mutations that are a result of polymerase errors that occur during enzymatic amplification of nucleic acids. The methods are based on the use of components of mismatch repair systems. The components and use of such systems is extensively described in "Methods of Analysis and Manipulation of DNA Utilizing Mismatch Repair Systems", WO 95/12688, which is incorporated herein, in its entirety, by reference. In most instances, sequences will be amplified by techniques familiar to those who practice the art, prior to application of the claimed methods.

PCR Amplification of DNA

PCR reactions were carried out to generate substrates for use in experiments described in Examples 1–3. The PCR primers utilized are indicated in the specific examples.

Unless otherwise noted, reactions (100 ul) contained 20 mM Tris-HCl (pH 8.2), 10 mM KCl, 6 mM $(NH_4)_2SO_4$, 4 mM $MgCl_2$, 0.1% Triton X-100, 10 μg/ml bovine serum albumin (BSA), 1 mM of each deoxyribonucleoside-5'-triphosphate (dNTP) (Pharmacia Biotech), 100 pmol of each primer, 5 μg T4 gene 32 protein (Boehringer Mannheim), 100 ng template DNA and 2.5 units of native Pfu DNA polymerase (Stratagene). Reactions in which synthetic products were uniformly labeled also contained 70 μCi of $[\alpha^{32}P]$dTTP (3000 Ci/mmol, DuPont/New England Nuclear). Reactions in which synthetic products were end-labeled contained 100 pmol of the appropriate primer labeled with T4 polynucleotide kinase (Amersham) and $[\gamma^{32}P]$ATP (3000 Ci/mmol, DuPont/New England Nuclear) as described (Sambrook et al., *Molecular Cloning a Laboratory Manual.* Cold Spring Harbor Laboratory Press, Cold Spring Harbor, N.Y., 1989). PCR reactions (15 cycles) were performed using a Perkin Elmer Gene Amp 96000 thermocycler with incubations at 94° C. for 15 sec, 60° C. for 15 sec and 72° C. for 90 sec, 3 min, 4 min or 6 min for amplification of 400 bp, 1.3 kb, 1.7 kb and 2.5 kb sequences respectively.

PCR reactions, in which Pfu, Vent (New England Biolabs) and Taq (Amersham) polymerases were compared, using buffer conditions recommended by the manufacturer. Reactions contained 1×buffer supplied with each polymerase as well as 200 μM of each dNTP, 100 pmol of each primer, 5 μg T4 gene 32 protein, 15 ng template DNA and 2.5 units of polymerase. The volume of each reaction was 100 μl. Reactions in which DNA was uniformly labeled contained 80 μCi of $[\alpha^{32}P]$dTTP. Reactions proceeded for 25 cycles with each cycle consisting of 15 sec at 94° C., 15 sec at 55° C. and 30 sec at 72° C.

To avoid introduction of contaminating DNA into PCR reactions, buffer components were made fresh daily and reactions were assembled in a laminar flow hood using filtered pipette tips. Products were extracted with phenol and ether, precipitated with ethanol and quantitated by an ethidium bromide dot method. Samples (0.5 ml of an appropriate dilution) and DNAs of known concentration were added to 8 μl of 1 μg/ml ethidium bromide and spotted onto plastic wrap. Ultraviolet-induced fluorescence was measured using a Photometrics cooled CCD imager. The concentration of PCR products was determined by comparison to the fluorescence of the standards.

MutHLS reactions

MutHLS reactions were carried out as follows in experiments described in Examples 1–3. Denaturation/reannealing reactions (20 μl) contained 2.5 μg of unlabeled PCR product, 0.5 μg of uniformly $^{32}$P labeled PCR product, 10 mM NaCL, 1 mM EDTA and 50 mM Hepes-KOH (pH 8.0). Freshly prepared 10N Na OH (0.6 μl) was added to a final concentration of 300 mM and the mixture was incubated at room temperature for five min. The solution was neutralized by addition of acetic acid to a final concentration of 300 mM, KCl to 100 mM and potassium phosphate (pH 7.4) to 100 mM, and the DNA hybridized at 65° C. for 30 min followed by 30 min at 37° C. Reactions were then bound to a silica matrix spin column (Pierce Xtreme DNA purification columns) and eluted with $dH_2O$ to remove PCR primers, dNTPs and salts.

Reactions (10 μl) (Au et al., supra) contained 50 mM Hepes-KOH (pH 8.0), 20 mM KCl, 4 mM $MgCl_2$, 1 mM dithiothreitol (DTT), 50 μg/ml BSA, 2 mM ATP, approximately 10,000 cpm of PCR DNA (50–200 ng), 250 ng MutS (Su et al., *Proc. Natl. Acad. Sci. USA,* 83:5057, 1986), 600 ng MutL (Grilley et al., *J. Biol. Chem.,* 264:1000, 1989) and 0.9 ng MutH (Welsh et al., *J. Biol. Chem.,* 262:15624, 1987).

DNA and buffer components were preincubated at 37° C. for 8 min, reactions initiated by adding a premixed solution of MutH, MutL and MutS and incubation continued for 15 min at 37° C. to produce single strand cleavage products. After addition of 0.5 μl of 0.5M EDTA and 20 μl of deionized formamide containing 0.05% bromophenol blue and 0.05% xylene cyanol, DNA products were analyzed by electrophoresis through 6% polyacrylamide in 89 mM Tris, 89 mM boric acid, 2 mM EDTA (final pH of 8.5) and 8M urea. DNA species were visualized by autoradiography and quantitated using a Molecular Dynamics Phosphorimager.

EXAMPLE 1
Polymerase errors during amplification account for d(GATC) cleavage of homohybrid products To determine whether the observed MutS-dependent d(GATC) cleavage of homohybrids was due to damage incurred during DNA preparation or to genetic variation introduced during PCR amplification, the dependence of the level of such cleavage on PCR reaction conditions was examined.

Phage f1 gene VII sequences of 1169 bp were amplified from the plasmid templates of Ivey-Hoyle et al. (Ivey-Hoyle et al., *J. Mol. Biol.*, 224:1039, 1992) for 10, 20 or 30 cycles using Pfu polymerase. Wild type lacI sequences 1360 bp in length were amplified from the plasmid clones of Matteson et al. (Matteson et al. *Nucleic Acids Res.*, 19:3499, 1991) for 25 cycles using Pfu, Vent or Taq polymerases. Both lacI and phage f1 gene VII sequences were amplified utilizing as the forward primer CAGAACTTTAAAAGTGCTCAT (SEQ. ID. NO. 1) and as the reverse primer ATGCAGCAAC-GAGACGTCACG (SEQ. ID. NO. 2). PCR products consisted of the gene fragments of interest as well as surrounding vector sequence. Both phage f1 gene VII sequences and lacI homohybrid molecules were prepared by a denaturation and reannealing step.

Figure 3A:
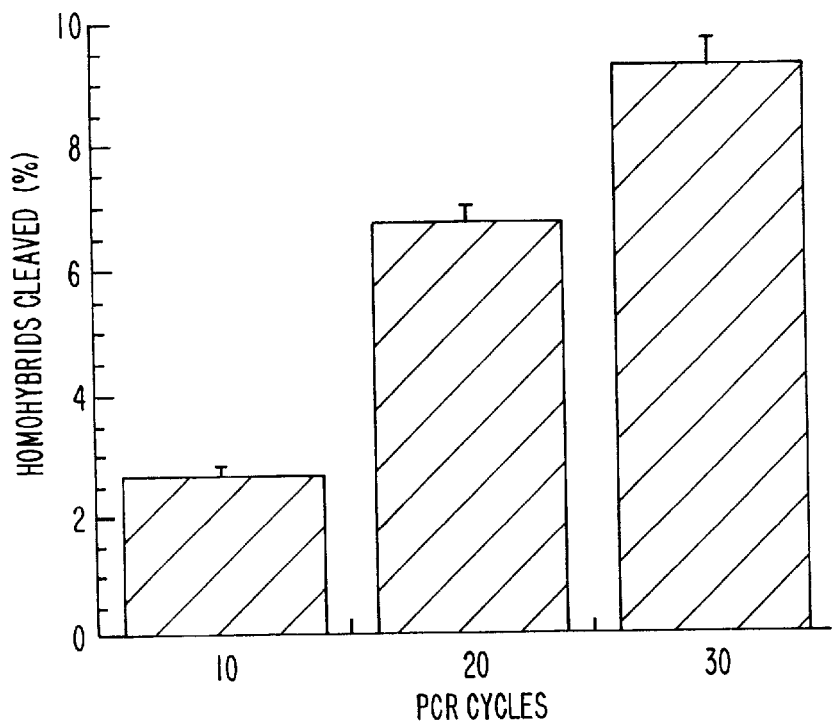
FIG. 3A is a graphic representation of the results of MutHLS cleavage of 1169 bp phage f1 gene VII homohybrids obtained after 10, 20 or 30 cycles of PCR amplification using Pfu polymerase. The x-axis represents number of PCR cycles. The y-axis represents homohybrids cleaved (%). Error bars indicate the standard error for four independent experiments.
Figure 3B:
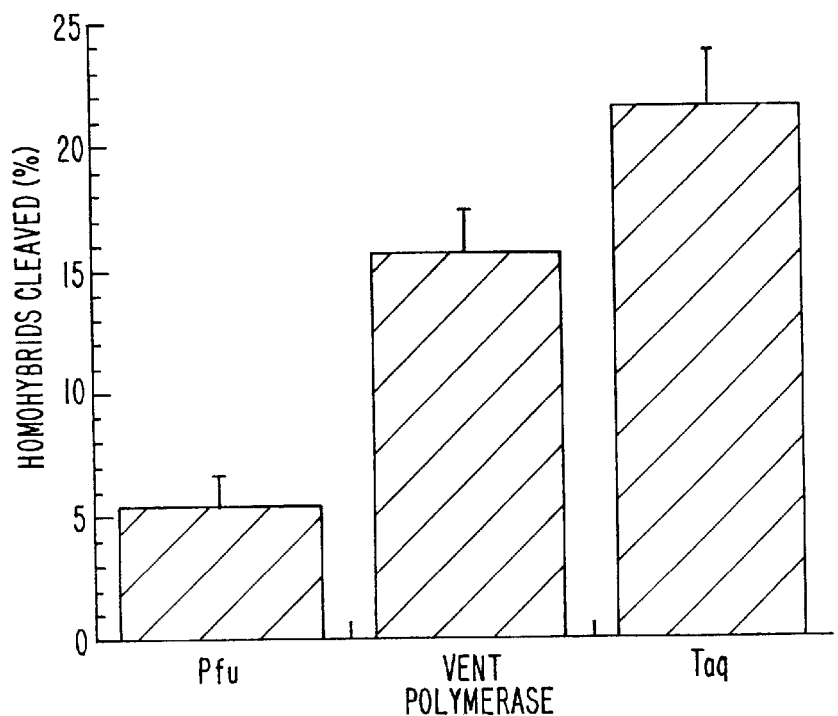
FIG. 3B represents the results of MutHLS cleavage of 1360 bp lacI homohybrids obtained after 25 cycles of amplification using Taq, Vent, or Pfu polymerases. The x-axis indicates the type of polymerase utilized. The y-axis represents homohybrids cleaved (%). Error bars indicate the standard error for four independent experiments.

The fraction of amplified phage f1 gene VII homohybrids cleaved by MutH increased with the number of cycles (See FIG. 3A), a finding consistent with either cycle-dependent DNA damage or polymerase-induced mutations. However, the degree of homohybrid cleavage was also found to depend on the polymerase used for PCR amplification. Thus, cleavage of amplified lacI homohybrids was highest when Taq polymerase was used for amplification, intermediate with Vent polymerase and lowest with Pfu polymerase (See FIG. 3B). These results parallel the error rates for these enzymes, with the lower fidelity of Taq polymerase due to absence of a 3' to 5' editing exonuclease (Lundberg et al., supra; Mattila et al, supra; Tindall et al., supra). Although a low level of template damage associated with thermal cycling cannot be excluded, these findings indicate that the majority of the homohybrid background signal is due to polymerase errors occurring during amplification.

Figure 4:
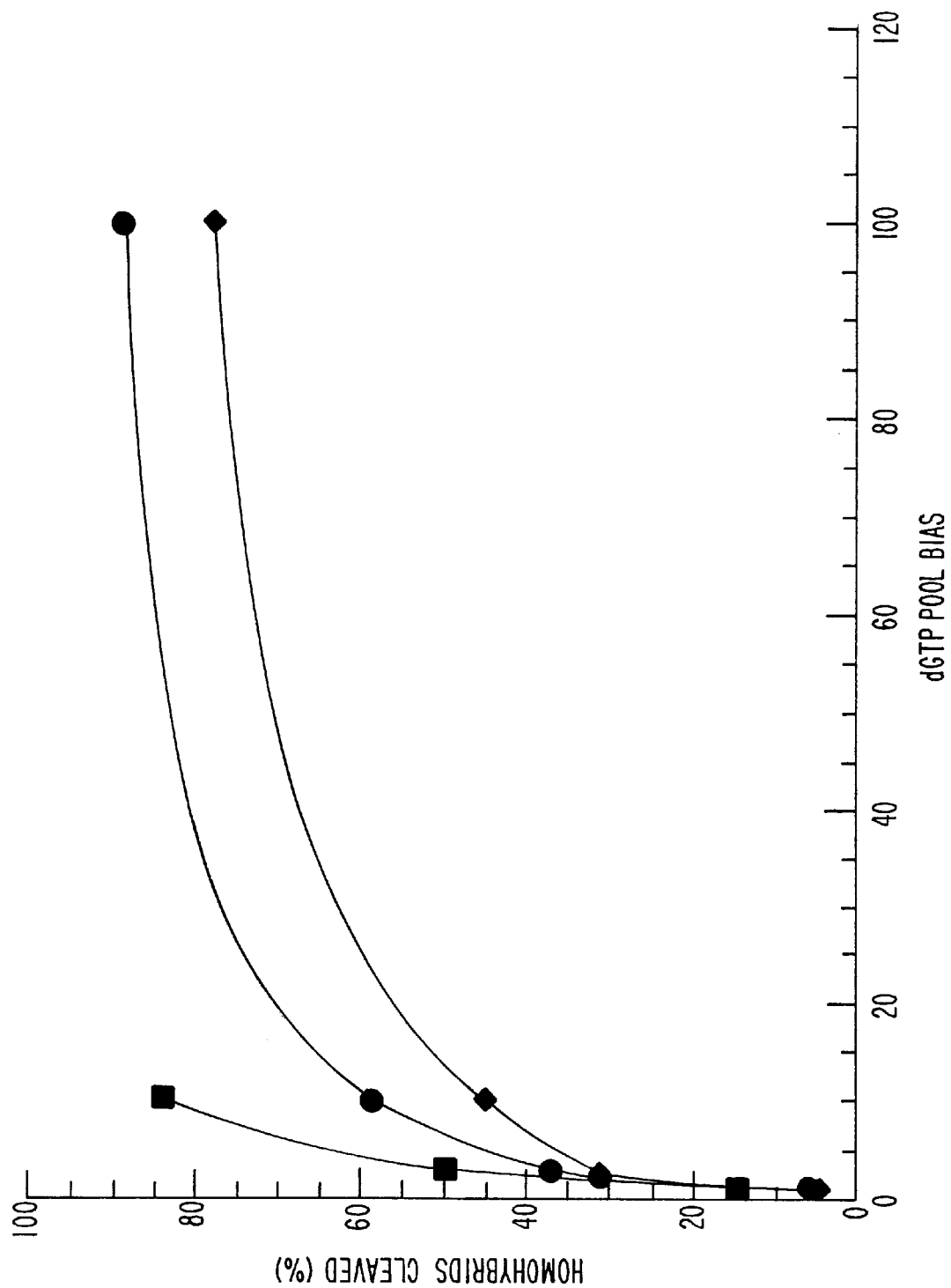
FIG. 4 is a graphic representation of the dependence of MutHLS cleavage on dNTP pool composition and polymerase used during amplification. The x-axis indicates the dGTP pool bias. The y-axis represents homohybrids cleaved (%). Polymerases utilized were: Pfu (♦), Vent (●) and Taq (■).

EXAMPLE 2
Use of dNTP pool bias during PCR amplification to determine detectability of nucleotide-substitution errors A dNTP pool imbalance leads to an increased error rate during in vitro synthesis by DNA polymerases (Kunkel et al., *J. Biol. Chem.*, 254:5718, 1979; Fersht, *Proc. Natl. Acad. Sci. USA*, 76:4946, 1979). This observation was exploited to test the utility of the MutHLS reaction for detection of PCR errors. For these experiments wild type lacI sequences 1360 bp in length were amplified for 15 cycles using Pfu, Vent or Taq polymerases under conditions of dGTP pool imbalance. Wild type lacI sequences were amplified from the plasmid clones of Matteson et al., (Matteson et al., *Nucleic Acids Res.*, 19:3499, 1991) utilizing as the forward primer CAGAACTTTAAAAGTGCTCAT (SEQ. ID. NO. 1) and as the reverse primer ATGCAGCAACGAGACGTCACG (SEQ. ID. NO. 2). PCR products consisted of the gene fragments of interest as well as surrounding vector sequence. Under equimolar conditions, each dNTP was present at 1 mM. The concentration of dGTP was 2 mM in all other reactions, and concentrations of the other three dNTPs were 667 μM 200 μM and 20 μM each. PCR products were denatured and reannealed, subjected to MutHLS cleavage, and products analyzed as previously described. As shown in FIG. 4, d(GATC) cleavage of homohybrids was dependent on the dGTP concentration bias. Homohybrids derived from amplification using Taq polymerase were subject to MutHLS-dependent d(GATC) cleavage to a greater degree than homohybrids amplified under the same conditions using Pfu and Vent polymerases. Negligible PCR product was obtained in reactions using Taq polymerase in which dGTP was present in a 100-fold molar excess over the other dNTPs. Since the enzyme lacks a 3' exonuclease activity, high levels of misincorporated dNTPs induce chain termination (Innis et al., *Proc. Natl. Acad. Sci. USA*, 85:9436, 1988). Likewise homohybrids amplified using Vent polymerase were cleaved to a greater extent than homohybrids amplified using Pfu polymerase (See FIG. 4). Polymerase misincorporation errors are therefore readily detectable by MutS-dependent d(GATC) cleavage.

Figure 5A:
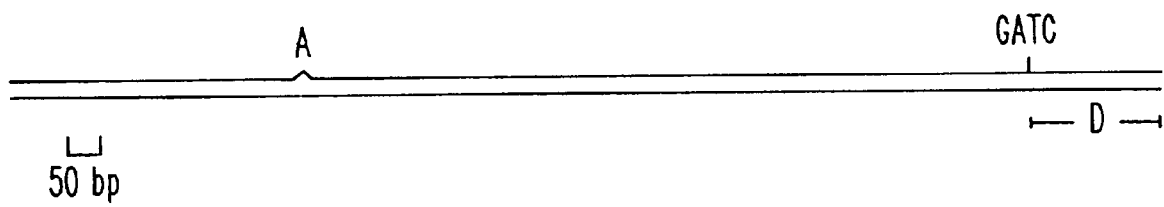
FIG. 5A is a schematic representation of a heterohybrid containing a base pair mismatch and an introduced dGATC site. Location of the single nucleotide insertion/deletion mutation is indicated as is the d(GATC) site, which are separated by about 1,000 bp.
Figure 5B:
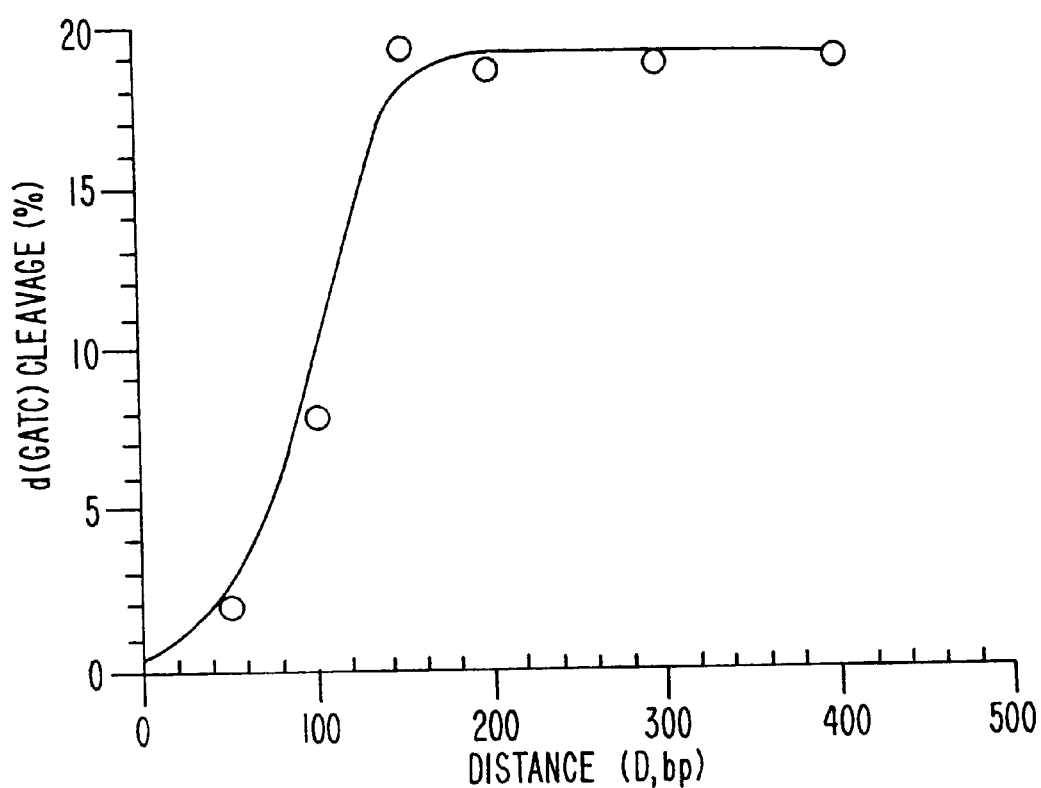
FIG. 5B is a graphic representation of the dependence of the efficiency of MutHLS cleavage of a heterohybrid on the distance between the dGATC site and the proximal DNA end. The x-axis represents distance in base pairs. The y-axis represents d(GATC) cleavage (%).

EXAMPLE 3
Dependence of the efficiency of cleavage by activated MutH on the distance between a d(GATC) site and the end of a DNA heterohybrid Although highly sensitive to mismatched base pairs, the MutHLS reaction can only be used for mutation screen if the sequence of interest contains a d(GATC) site. To determine the feasibility of introducing a d(GATC) site into a PCR primer in order to screen sequences lacking such a site, we have evaluated the dependence of the reaction on the distance of a d(GATC) site from a DNA end (See FIG. 5A). Heterohybrids were prepared after amplification of the replicative form of phage f1MR21 and f1MR22 (which contains one extra nucleotide relative to phage f1MR21)for 15 cycles using nested reverse PCR primers GATAAGAGGT-CATTTTTGCGG (SEQ. ID. NO. 3) (1470 bp PCR product); AGACCGGAAGCAAACTCCAAC (SEQ. ID. NO. 4) (1528 bP PCR product); GCCCGAAAGACTTCAAATATC (SEQ. ID. NO. 5) (1578 bp PCR product); TTATAGTCA-GAAGCAAAGCGG (SEQ. ID. NO. 6) (1624 bp PCR product); GGATAGCGTCCAATACTGCGG (SEQ. ID. NO. 7) (1743 bp PCR product); ATCATAACCCTCGTTTAC-CAG (SEQ. ID. NO. 8) (1845 bp PCR product) and the same forward primer CCAGCAAGGCCGATAGTTTGA (SEQ. ID. NO. 9). Phage f1MR22 was constructed by the insertion of a synthetic oligonucleotide duplex (Parsons et al., *Cell*, 75:1227, 1993) into the replicative form of phage f1MR1 (Su et al., *supra*). PCR products were amplified, and heterohybrids were prepared by denaturing and reannealing a mixture of PCR products obtained from the mutant and wild type DNA. Heterohybrids were subject to MutHLS reaction and analyzed as previously described. Maximum cleavage observed with these heterohybrids was 20%, perhaps reflecting the large (1,000 bp) distance between the mutation and the d(GATC) site. As shown in FIG. 5B, the efficiency of mismatch-provoked cleavage increased with increasing distance of the d(GATC) site from the proximal end in the range of 50–150 bp reaching a maximum at the latter distance. These results suggest that a PCR primer with a d(GATC) site 50–100 nucleotides from an end would prove sufficient for the purpose of amplification and subsequent mutation screen using MutH, MutL and MutS.

EXAMPLE 4
Removal of molecules containing a polymerase-generated mutation utilizing MutHLS reaction followed by gel electrophoresis A population of molecules that have been enzymatically amplified is subject to denaturation/reannealing reactions. A solution of amplified product (20 μl) is made to have a concentration of 10 mM NaCL, 1 mM EDTA and 50 mM Hepes-KOH (pH 8.0). Freshly prepared 10N NaOH is added to a final concentration of 300 mM and the mixture is incubated at room temperature for five minutes. The solution is neutralized by addition of acetic acid to a final concentration of 300 mM, KCl to 100 mM and potassium phosphate (pH 7.4) to 100 mM, and the DNA hybridized at 65° C. for 30 minutes followed by 30 minutes at 37° C. Reactions are then bound to a silica matrix spin column (Pierce Xtreme DNA purification columns) and eluted with dH20 to remove PCR primers, dNTPs and salts.

MutHLS reactions are carried out (10 μl) or adjusted for volume as necessary containing 50 mM Hepes-KOH (pH 8.0), 20 mM KCl, 4 mM $MgCl_2$, 1 mM dithiothreitol (DTT), 50 mg/ml BSA, 2 mM ATP, PCR DNA (50–200 ng), 500 ng MutS, 1200 ng MutL and 1.8 ng MutH. DNA and buffer components are preincubated at 37° C. for 8 minutes, reactions are initiated by adding a premixed solution of MutH, MutL, and MutS and incubation continued for 45 minutes at 37° C. Reactions are supplemented with additional MutS (500 ng), MutL (1200 ng) and MutH (1.8 ng) and incubated at 37° for an additional 45 min. Double strand cleavage products are produced.

After quenching the reaction with EDTA (6 mM final concentration) and SDS (0.1% final concentration), the uncleaved fraction, enriched in mutation-free sequence, can be isolated by electrophoresis through non-denaturing agarose or polyacrylamide gels, depending on DNA size. The desired fragment can be isolated from the gel by methods well-known in the field (Ausubel, F.M. et al. *Current protocols in Molecular Biology*. John Wiley and Sons Inc.).

EXAMPLE 5
Rending molecules containing a polymerase generated mutation inert to further amplification A population of DNA molecules is enzymatically amplified and subjected to denaturation and reannealing and MutHLS double strand cleavage as in Example 4. DNA products (about 250 ng) are incubated in a 50 μl reaction containing 50 mM Tris-HCl (pH 7.5), 10 mM $MgCl_2$, 1 mM DTT, 50 μg/ml BSA, 25 μM of each dideoxynucleoside-5'-triphosphate (ddGTP, ddATP, ddCTP, and ddTTP), and one unit of exonuclease-free Klenow DNA polymerase at 37° C. for 3 hours. The reaction is quenched by addition of EDTA to 20 mM, and extraction with phenol then ether. After removal of unincorporated ddNTPs using a silica matrix spin column (See Example 4), the resulting population of DNA molecules may then be subjected to additional rounds of PCR as required.

EXAMPLE 6
Removal of molecules containing a polymerase-generated mutation utilizing MutHLS reaction followed by enzymatic degradation A population of DNA molecules is enzymatically amplified using primers with 5'-OH termini and are subjected to denaturation and reannealing and MutHLS double strand cleavage as in Example 4. DNA products (50 ng) are then incubated in 100 μl reactions containing 67 mM glycine-NaOH (pH 9.4), 25 mM $MgCl_2$, 50 μg/ml BSA, and 2.5 units of lambda exonuclease at 37° C. for 60 min. Exonuclease I (0.1 unit) is then added and reaction continued at 37° C. for an additional 30 min. Reactions are terminated by addition of EDTA to 20 mM, and reactions are extracted to remove the exonucleases with phenol and then ether. The population is then subject to additional rounds of amplification as required.

EXAMPLE 7
Determination of the fraction of an enzyzymatically amplified DNA population that contains a polymerase-generated mutation Specific primers, PCR cycles and conditions, and the polymerase utilized are determined by the specific sequence to be amplified and the objectives of the amplification procedure based on techniques and methods familiar to those who practice the art. MutHLS reactions (single or double strand cleavage), separation of cleaved and uncleaved molecules, and quantitation can be carried out as previously described. Other labeling, visualization, and quantitation techniques utilized with nucleic acids, that are known to those who practice the art, such as fluorescent labeling and staining with ethidium bromide, are suitable for use in this aspect of the invention.

EXAMPLE 8
Determination of the Efficiency of MutHLS Treatment for Removal of Molecules Containing Mutation from PCR Product Pools The genomes of filamentous bacteriophages are composed entirely of essential genes; however, a noncoding region between genes II and IV exists in which foreign DNA may be inserted. This region contains a cis-acting signal for packaging and orientation of DNA within bacteriophage particles, sites for the initiation and termination of DNA synthesis, and a signal for p-independent termination of transcription. The presence of foreign DNA segments within this region can disrupt the cis-acting elements that control replication. All filamentous phage vectors in common use therefore contain mutations in genes II or V that compensate for such disruption.

Messing and coworkers (Messing, J. New M13 Vectors for Cloning, *Methods Enzymol.*, 101:20–78, 1983) created a series of bacteriophage M13-lac hybrid vectors by insertion of the regulatory sequences and the coding information for the first 146 amino acids of the *E. coli* β-galactosidase gene (lacZ) into the intergenic region between genes II and IV of M13. The host cells for these M13 hybrid phage contain an F' plasmid with a β-galactosidase gene teat is defective due to the fact that it encodes an enzymatically inactive polypeptide lacking amino acids 11–41. The amino terminal fragment of β-galactosidase produced in cells infected with an M13-lac hybrid vector associates with the defective host polypeptide to form an enzymatically active protein (this is called α-complementation). This has allowed development of a color test to distinguish vectors that have a functional as opposed to a genetically inactive β-galactosidase gene fragment. When plated on hosts carrying the appropriate F' episome, vectors encoding the wild type β-galactosidase gene fragment will form blue plaques when the medium contains the inducer IPTG and the chromogenic β-galactosidase substrate, X-GAL. By contrast, disruption of the phage lacZ region by mutation or by insertion of foreign DNA blocks α-complementation and results in pale blue or colorless plaques.

This principle has been exploited for the development of an assay for assessment of the replication fidelity of DNA polymerases (Benenek, K. and Kunkel, T. A. Analyzing Fidelity of DNA Polymerases. *Methods Enzymol.*

262:217–232, 1995). In this method an M13 substrate was constructed which contained a single-strand gap spanning the phage lacZ sequence. The gap was then filled by a polymerase of interest, the reaction products introduced into E. coli host cells that support α-complementation, and plated in the presence of X-GAL and IPTG. If the gap-filling DNA synthesis is error-free, the β-galactosidase peptide produced will complement the defective β-galactosidase of the host, and X-GAL will be hydrolyzed in these cells to produce blue plaques. Pale blue or clear plaques are produced when errors made during the gap-filling reaction result in production of a β-galactosidase polypeptide of altered amino acid sequence that is incapable of complementation.

Figure 6:
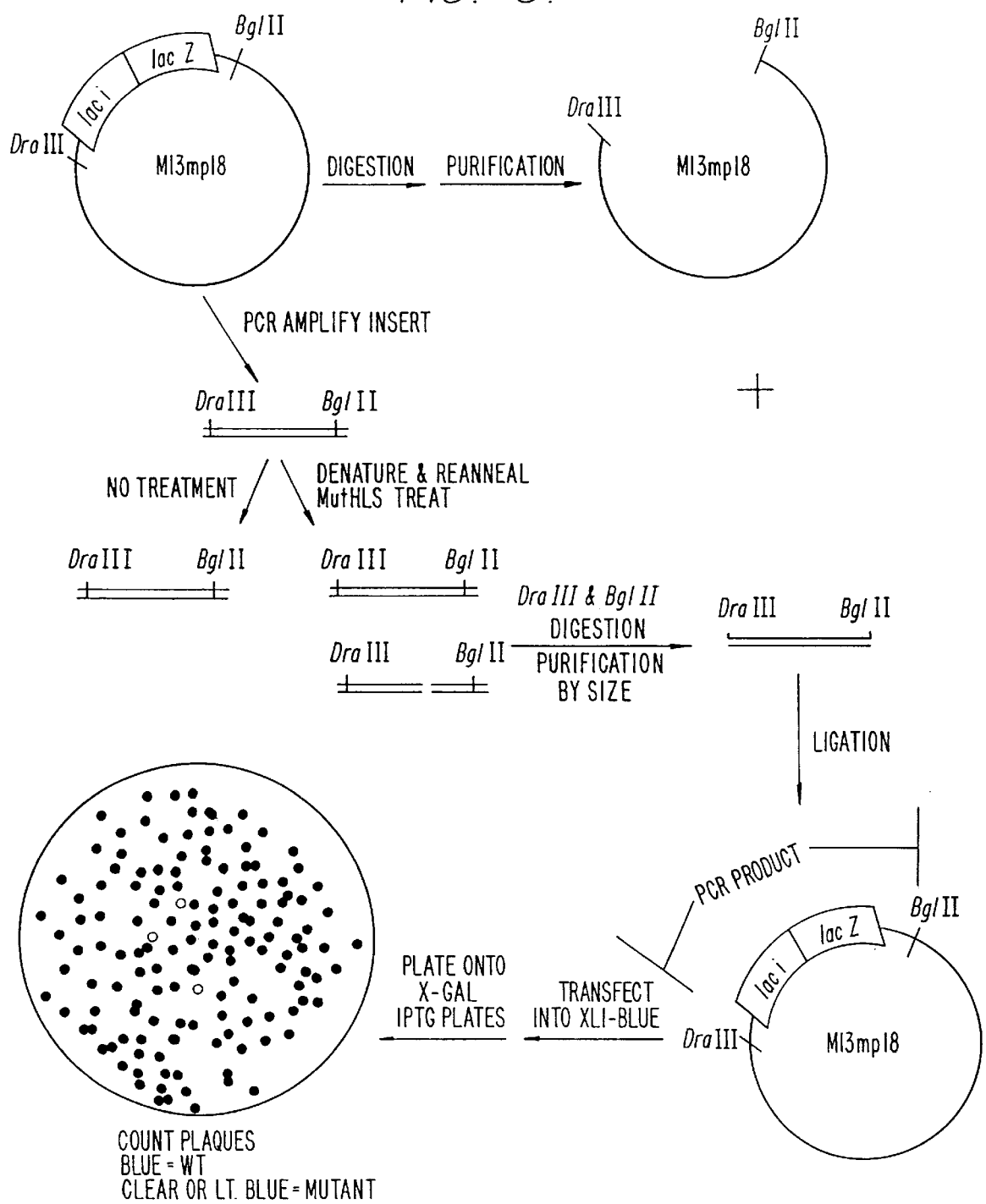
FIG. 6 is a schematic representation of the experimental design for assessing the efficiency of MutHLS treatment for removal of sequences containing polymerase-induced mutations that occur during the process of PCR.

A variation of this fidelity assay was used to assess the efficiency of MutHLS treatment for removal of sequences containing polymerase-induced mutations that occur during the process of PCR. As outlined in FIG. 6, a region of M13mp18 spanning the β-galactosidase gene fragment was amplified using the polymerase chain reaction and products were denatured and reannealed. MutHLS treatment was then used to cleave both strands of molecules containing point mutations or small insertions and deletions, producing double-strand breaks in such molecules. Full-length products were then isolated and ligated into an M13mp18 molecule to which the region corresponding to the PCR product had been removed, thus replacing the wild type M13mp18 fragment with the corresponding PCR product. Ligation products were then transfected into E. coli cells and plated in the presence of IPTG, X-GAL, and an appropriate host strain. The presence of dark blue plaques indicates clones containing wild-type β-galactosidase gene fragments and pale blue or clear plaques indicates clones containing mutations in the β-galactosidase gene. The proportion of pale blue and clear plaques to total plaques in molecules treated with MutHLS compared to the corresponding proportion in untreated molecules indicates the degree of reduction of the presence of mutant sequences.

PCR Amplification of DNAs

A 1611 base pair (bp) fragment of M13mp18 was amplified which spanned the 390 bp β-galactosidase gene segment of interest. With respect to the viral strand sequence, a Dra III site is located 256 bp from the 5' end of the PCR product and a Bgl II site is located 134 bp from the 3' end of the PCR product (see FIG. 6). PCR reactions (100 $\mu$l) contained 50 mM KCl, 10 mM Tris-HCl (pH 8.3), 2 mM $MgCl_2$, 200 $\mu$M each dNTP (Pharmacia), 100 pmol each primer (21 nucleotides long with 5' -OH termini; Oligos Etc., Guliford, Conn.), 5 $\mu$g of T4 gene 32 protein (Boehringer Mannheim), 50 ng template DNA (M13mp18), and 2.5 units of AmpliTaq DNA polymerase (Perkin Elmer). The sequence of the forward primer was 5'-TTA TAC GTG CTC GTC AAA GCA-3' (SEQ. ID. NO. 10) corresponding to nucleotides 5458–5478 in M13mp18 and the sequence of the reverse primer was 5'-AAT GCC TGA GTA ATG TGT AGG-3' (SEQ. ID. NO. 11) corresponding to nucleotides 7048–7069 of M13mp18. Reactions (30 cycles) were performed using a Perkin Elmer Gene Amp 9600 thermocycler with incubations at 94° C. for 15 sec, 60° C. for 15 sec, and 72° C. for 1 min. Products were denatured and reannealed immediately following amplification by heating to 95° C. for 1 min and incubation at 65° C. for 60 min followed by incubation at 37° C. for 30 min. EDTA was then added to 20 mM and reactions were extracted with phenol followed by binding to a silica matrix spin column (Pierce Xtreme DNA purification columns) and eluted with distilled H20 to remove PCR primers, dNTPs, and salts. Products were quantitated by an ethidium bromide dot method as follows: Samples (2.0 $\mu$l of an appropriate dilution) and DNAs of known concentration were added to 8 $\mu$l of 1 $\mu$g/ml ethidium bromide and spotted onto plastic wrap. UV-induced fluorescence was measured using a Photometrics cooled charge-coupled device imager. The concentration of PCR products was determined by comparison to the fluorescence of the standards.

MutHLS Reactions

Reactions (50 $\mu$l total) were assembled as follows: 20 $\mu$l of 125 mM HEPES (pH 8.0), 50 mM KCl, 2.5 mM dithiothreitol (DTT), 125 $\mu$g/ml bovine serum albumin (BSA), 5 mM ATP, 10 mM $MgCl_2$, and 1 $\mu$g PCR DNA were preincubated at 37° C. for 8 min. Reactions were then initiated by adding 30 $\mu$l of a premixed solution of 5 $\mu$g MutS (Su, S.-S. and Modrich, P., Proc. Natl. Acad. Sci. U.S.A. 83, 5057–5061, 1986), 12 $\mu$g MutL (Grilley, M., Welsh, K. M., Su, S.-S. & Modrich, P., J. Biol. Chem. 264:1000–1004, 1989) and 18 ng of MutH (Welsh, K. M., Lu, A.-L., Clark, S. & Modrich, P., J. Biol. Chem. 262:15624–15629, 1987) in 20 mM potassium phosphate (pH 7.4), 50 mM KCl, 0.1 mM EDTA, 1 mM DTT, and 1 mg/ml BSA. Incubation was continued for 45 min at 37° C. An additional 30 $\mu$l of a premixed solution of 5 $\mu$g MutS, 12 $\mu$g MutL, and 18 ng MutH in the same buffer described above was then added as well as 3 $\mu$l of a 10×buffer solution containing 500 mM HEPES (pH 8.0), 200 mM KCl, 10 mM DTT, 20 mM ATP, and 40 mM $MgCl_2$. Incubation was continued at 37° C. for 45 min. An additional 30 $\mu$l of a premixed solution of 5 $\mu$g MutS, 12 $\mu$g MutL, and 18 ng MutH in the same buffer as described above was then added as well as 3 $\mu$l of a 10×buffer solution containing 500 mM HEPES (pH 8.0), 200 mM KCl, 10 mM DTT, 20 mM ATP, and 40 mM $MgCl_2$. Incubation was continued at 37° C. for an additional 45 min. Reactions were terminated by addition of EDTA to 10 mM, and extracted with phenol followed by extraction with ether. DNA was then bound to a Qiagen column (QIAquick spin column) and eluted with distilled $H_2O$ to concentrate the DNA and to remove proteins, salts, and all other reaction components.

Restriction Digestion and Gel Purification

After MutHLS treatment the DNA was digested with Dra III and Bgl II in a 20 $\mu$l reaction containing 1 $\mu$g DNA, 100 $\mu$M NaCl, 50 mM Tris-HCl (pH7.5), 10 mM $MgCl_2$, 1 mM DTT, 100 $\mu$g/ml Bovine Serum Albumin, 4 units Bgl II (New England Biolabs), and 10 units Dra III (Amersham). Reaction components were incubated at 37° C. for 2 hr and the reaction was terminated by addition of EDTA to 10 mM. Products were precipitated with ethanol followed by electrophoresis through 1% agarose in 40 mM Tris-acetate, 1 mM EDTA (final pH 7.5). The full-length band (corresponding to the Dra III/Bgl II fragment of M13mp18) was recovered using a Gene Clean Kit (Bio 101) according to recommendations of the manufacturer. The recovered DNA was quantitated using the ethidium bromide dot method described above.

Ligation Reactions

The PCR product corresponding to the Dra III/Bgl II fragment of M13mp18, recovered after MutHLS treatment, Dra III/Bgl II digestion, and gel purification, was ligated into an M13mp18 derivative in which the Dra III/Bgl II fragment had been removed. The ligation reactions (20 $\mu$l) contained 50 ng PCR DNA fragment, 50 ng M13mp18 (without the Dra III/Bgl II fragment), 66 mM Tris-HCl (pH 7.6), 6.6 mM $MgCl_2$, 10 mM DTT, 66 $\mu$M ATP, and 0.5 Weiss unit of T4 DNA ligase. Reactions were incubated at 16° C. for 12–16 hrs.

Transfections

Ligation reaction products were transfected into XL2-Blue Ultracompetent Cells (Stratagene) following the included protocol. An aliquot (50 μl) of the transfection reaction was added to a tube at 49° C. containing 4 mls of Luria-Bertani soft agar, 4 mg of X-GAL (Amersham), and 800 μg of IPTG (Amersham). Then 200 μl of a log-phase culture of XLI-Blue was added. The soft agar mixture was poured onto a Luria-Bertani plate and allowed to solidify. Plates were incubated at 37° C. 12–16 hrs, and 3,000 to 12,000 plaques then scored according to color as mutant or wild type.

Results obtained with three independent samples of PCR-amplified DNA are summarized in Table 1. As noted above, dark blue plaques indicate the presence of a clone containing a wild type β-galactosidase gene fragment and pale blue or clear plaques indicate the presence of a clone containing a mutation somewhere within this region. This assay detects single base substitution mutations at 114 positions within the 390 bp β-galactosidase a fragment, as well as single nucleotide frameshifts at 150 positions (Eckert, K. A., and Kunkel, T. A., *Nucl. Acids Res.* 18:3739–3744, 1990). As shown in Table 1, the MutHLS double strand cleavage reaction reduced the incidence of mutant plaques by 88–93%.

TABLE 1

| Experiment | Mutant Plaques | Wild Type Plaques | Mutant Fraction % |
|---|---|---|---|
| −HLS 1 | 127 | 3,546 | 3.58 |
| −HLS 2 | 204 | 5,591 | 3.65 |
| −HLS 3 | 213 | 6,947 | 3.07 |
| +HLS 1 | 23 | 5,191 | 0.44 |
| +HLS 2 | 31 | 11,339 | 0.27 |
| +HLS 3 | 45 | 11,941 | 0.38 |

Mutant Frequency=100×[number of mutant plaques/total number of plaques]

Other embodiments are within the following claims.

What is claimed is:

1. Method for removing DNA molecules containing one or more polymerase-generated mutations in a population of DNA duplexes that have been enzymatically amplified using primers containing 5'-hydroxyl termini comprising the steps of:

denaturing and reannealing said population of DNA duplexes, contacting said reannealed DNA duplexes with a mismatch repair system such that each strand in DNA duplexes containing a base pair mismatch is cleaved, and further contacting said population of reannealed DNA duplexes with exonucleases so that said DNA duplexes containing a base pair mismatch are enzymatically degraded to single nucleotides or dinucleotides.

2. The method of claim 1, wherein said mismatch repair system comprises components of the methyl-directed mismatch repair system of E. coli and includes the MutS, MutL, and MutH proteins.

3. The method of claim 1, wherein said exonucleases comprise an exonuclease that preferentially acts on duplexes with a 5' phosphate, and an exonuclease that degrades single-stranded DNA.

4. Method for rendering inert to further amplification DNA molecules containing one or more polymerase-generated mutations in a population of enzymatically amplified DNA duplexes comprising the steps of:

denaturing and reannealing said population of DNA duplexes, contacting said reannealed DNA duplexes with a mismatch repair system such that each strand is cleaved in DNA duplexes containing a base pair mismatch, and, further contacting said cleaved DNA duplexes with dideoxynucleoside-5'-triphosphates and an exonuclease-free DNA polymerase.

5. The method of claim 4, wherein said mismatch repair system comprises components of the methyl-directed mismatch repair system of E. coli and includes the MutS, MutL, and MutH proteins and the dideoxynucleoside-5'-triphosphate is dideoxyguanosine-5'-triphosphate.

6. Method for detecting the presence of DNA polymerase-generated mutations in a population of enzymatically amplified DNA duplexes, wherein said duplexes lack a sequence subject to mismatch provoked endonucleolytic cleavage, wherein said method comprises comprising the steps of:

enzymatically amplifying a population of DNA molecules utilizing primers containing a sequence subject to mismatch provoked endonucleolytic cleavage, wherein said sequence subject to mismatch provoked endonucleolytic cleavage is at least 50 to 150 nucleotides from an end of said primer, denaturing and reannealing said population of DNA duplexes, contacting said reannealed DNA duplexes with a mismatch repair system under conditions such that an endonucleolytic incision is introduced in at least one strand of a duplex containing a polymerase generated mutation, and detecting the product of said endonucleolytic incision as an indication of the presence of polymerase generated mutations.

7. The method of claim 6 wherein said sequence subject to mismatch provoked endonucleolytic cleavage is a d(GATC) site.

8. The method of claim 6 wherein the detection of the product of said endonucleolytic incision is by altered electrophoretic mobility under denaturing conditions.

9. The method of claim 6, wherein said mismatch repair system comprises components of the methyl-directed mismatch repair system of E. coli and includes the MutS, MutL, and MutH proteins.

10. Method for removing DNA molecules containing one or more polymerase-generated mutations in a population of enzymatically amplified DNA duplexes, wherein said DNA is lacking a sequence subject to mismatch provoked endonucleolytic cleavage, wherein said method comprises the steps of:

enzymatically amplifying a population of DNA molecules utilizing primers containing a sequence subject to mismatch provoked endonucleolytic cleavage, wherein said sequence subject to mismatch provoked endonucleolytic cleavage is at least 50 to 150 nucleotides from an end of said primer, denaturing and reannealing said population of DNA duplexes, contacting said reannealed DNA duplexes with a mismatch repair system under conditions such that each strand is cleaved in a DNA duplex containing a polymerase generated mutation, and separating said cleaved DNA duplexes from uncleaved DNA duplexes.

11. A kit for amplifying DNA molecules and for removing DNA molecules containing one or more polymerase-generated mutations in a population of enzymatically amplified DNA duplexes comprising:

primers with 5'-hydroxyl termini, components of a mismatch repair system, and exonucleases that enzymatically degrade DNA duplexes.

12. A kit for rendering inert to further amplification DNA molecules containing one or more polymerase-generated mutations in a population of enzymatically amplified DNA duplexes comprising:

components of a mismatch repair system, a dideoxynucleoside-5'-triphosphate, and an exonuclease-free DNA polymerase.

13. Kit for amplifying DNA molecules lacking a sequence subject to mismatch provoked endonucleolytic cleavage and detecting or removing DNA molecules containing one or more polymerase-generated mutations in a population of enzymatically amplified DNA duplexes comprising:

primers containing sequence subject to mismatch provoked endonucleolytic cleavage, wherein said sequence subject to mismatch provoked endonucleolytic cleavage is at least 50 to 150 nucleotides from an end of said primer, and components of a mismatch repair system.

14. A kit for removing DNA molecules containing one or more polymerase-generated mutations in a population of enzymatically amplified DNA duplexes comprising:

components of a mismatch repair system, and exonucleases that enzymatically degrade DNA duplexes to single nucleotides or dinucleotides.

15. The kit of either of claims 11 or 14, wherein said exonucleases comprise an exonuclease that preferentially acts on duplexes with a 5' phosphate, and an exonuclease that degrades single-stranded DNA.

16. The kit of either of claims 11 or 14, wherein said exonucleases are lambda exonuclease and Exonuclease I.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH:           21 base pairs
      (B) TYPE:             nucleic acid
      (C) STRANDEDNESS:     single
      (D) TOPOLOGY:         linear (xi) SEQUENCE DESCRIPTION: SEQ ID NO: 1:

CAGAACTTTA AAAGTGCTCA T                                      21

(2) INFORMATION FOR SEQ ID NO: 2:

(i) SEQUENCE CHARACTERISTICS:
      (A) LENGTH:           21 base pairs
      (B) TYPE:             nucleic acid
      (C) STRANDEDNESS:     single
      (D) TOPOLOGY:         linear (xi) SEQUENCE DESCRIPTION: SEQ ID NO: 2:

ATGCAGCAAC GAGACGTCAC G                                      21

(2) INFORMATION FOR SEQ ID NO: 3:

(i) SEQUENCE CHARACTERISTICS:
      (A) LENGTH:           21 base pairs
      (B) TYPE:             nucleic acid
      (C) STRANDEDNESS:     single
      (D) TOPOLOGY:         linear (xi) SEQUENCE DESCRIPTION: SEQ ID NO: 3:

GATAAGAGGT CATTTTTGCG G                                      21

(2) INFORMATION FOR SEQ ID NO: 4:

(i) SEQUENCE CHARACTERISTICS:
      (A) LENGTH:           21 base pairs
      (B) TYPE:             nucleic acid
      (C) STRANDEDNESS:     single
      (D) TOPOLOGY:         linear (xi) SEQUENCE DESCRIPTION: SEQ ID NO: 4:

AGACCGGAAG CAAACTCCAA C                                              21

(2) INFORMATION FOR SEQ ID NO: 5:

(i) SEQUENCE CHARACTERISTICS:
        (A) LENGTH:             21 base pairs
        (B) TYPE:               nucleic acid
        (C) STRANDEDNESS:       single
        (D) TOPOLOGY:           linear (xi) SEQUENCE DESCRIPTION: SEQ ID NO: 5:

GCCCGAAAGA CTTCAAATAT C                                              21

(2) INFORMATION FOR SEQ ID NO: 6:

(i) SEQUENCE CHARACTERISTICS:
        (A) LENGTH:             21 base pairs
        (B) TYPE:               nucleic acid
        (C) STRANDEDNESS:       single
        (D) TOPOLOGY:           linear (xi) SEQUENCE DESCRIPTION: SEQ ID NO: 6:

TTATAGTCAG AAGCAAAGCG G                                              21

(2) INFORMATION FOR SEQ ID NO: 7:

(i) SEQUENCE CHARACTERISTICS:
        (A) LENGTH:             21 base pairs
        (B) TYPE:               nucleic acid
        (C) STRANDEDNESS:       single
        (D) TOPOLOGY:           linear (xi) SEQUENCE DESCRIPTION: SEQ ID NO: 7:

GGATAGCGTC CAATACTGCG G                                              21

(2) INFORMATION FOR SEQ ID NO: 8:

(i) SEQUENCE CHARACTERISTICS:
        (A) LENGTH:             21 base pairs
        (B) TYPE:               nucleic acid
        (C) STRANDEDNESS:       single
        (D) TOPOLOGY:           linear (xi) SEQUENCE DESCRIPTION: SEQ ID NO: 8:

ATCATAACCC TCGTTTACCA G                                              21

(2) INFORMATION FOR SEQ ID NO: 9:

(i) SEQUENCE CHARACTERISTICS:
        (A) LENGTH:             21 base pairs
        (B) TYPE:               nucleic acid
        (C) STRANDEDNESS:       single
        (D) TOPOLOGY:           linear (xi) SEQUENCE DESCRIPTION: SEQ ID NO: 9:

CCAGCAAGGC CGATAGTTTG A                                              21

(2) INFORMATION FOR SEQ ID NO: 10:

(i) SEQUENCE CHARACTERISTICS:
        (A) LENGTH:             21 base pairs
        (B) TYPE:               nucleic acid
        (C) STRANDEDNESS:       single
        (D) TOPOLOGY:           linear (xi) SEQUENCE DESCRIPTION: SEQ ID NO: 10:

-continued

```
TTATACGTGC TCGTCAAAGC A                                              21

(2) INFORMATION FOR SEQ ID NO:     11:

(i) SEQUENCE CHARACTERISTICS:
        (A) LENGTH:         21 base pairs
        (B) TYPE:           nucleic acid
        (C) STRANDEDNESS:   single
        (D) TOPOLOGY:       linear (xi) SEQUENCE DESCRIPTION: SEQ ID NO:    11:

AATGCCTGAG TAATGTGTAG G                                              21
```